(12) United States Patent
Nugue et al.

(10) Patent No.: US 8,959,770 B2
(45) Date of Patent: Feb. 24, 2015

(54) PROCESS FOR MANUFACTURING A LAMINATED GLAZING UNIT

(75) Inventors: Jean-Clement Nugue, Lamorlaye (FR); Fabien Levasseur, Marest sur Matz (FR); Romain Decourcelle, Compiegne (FR)

(73) Assignee: Saint-Gobain Glass France, Courbevoie (FR)

( * ) Notice: Subject to any disclaimer, the term of this patent is extended or adjusted under 35 U.S.C. 154(b) by 532 days.

(21) Appl. No.: 13/381,530

(22) PCT Filed: Jun. 30, 2010

(86) PCT No.: PCT/EP2010/059270
§ 371 (c)(1),
(2), (4) Date: Feb. 8, 2012

(87) PCT Pub. No.: WO2011/000862
PCT Pub. Date: Jan. 6, 2011

(65) Prior Publication Data
US 2012/0135248 A1    May 31, 2012

(30) Foreign Application Priority Data

Jun. 30, 2009  (FR) .................................. 09 54466

(51) Int. Cl.
*B32B 17/10*  (2006.01)

(52) U.S. Cl.
CPC .. *B32B 17/10036* (2013.01); *G01N 2203/0023* (2013.01); *G01N 2203/0092* (2013.01)
USPC ................. 29/890.033; 428/212; 428/424.6; 428/688; 156/64; 156/99; 156/100; 181/290

(58) Field of Classification Search
USPC .......... 29/890.033; 428/212, 424.6, 688, 426, 428/411.1; 156/64, 99, 100; 264/339
See application file for complete search history.

(56) References Cited

U.S. PATENT DOCUMENTS

| 3,697,364 A | 10/1972 | Boustany et al. |
| 4,749,430 A | 6/1988 | Samuelson et al. |

(Continued)

FOREIGN PATENT DOCUMENTS

| FR | 2 086 121 | 12/1971 |
| FR | 2 616 908 | 12/1988 |

OTHER PUBLICATIONS

International Search Report Issued Sep. 15, 2010 in PCT/EP10/59270 Filed Jun. 30, 2010.

*Primary Examiner* — David Bryant
*Assistant Examiner* — Jun Yoo
(74) *Attorney, Agent, or Firm* — Oblon, Spivak, McClelland, Maier & Neustadt, L.L.P.

(57) ABSTRACT

A process for manufacturing a laminated glazing unit so that it withstands a predetermined load, in which the unit includes at least one substrate having a glass function and at least one layer of polymeric interlayer. The process: obtains viscoelastic behavior of constituent material of the interlayer; calculates maximum value of at least one quantity representative of the loading resistance of the laminated glazing unit subjected to the predetermined load; adjusts dimensions of the unit such that the calculated maximum value of the quantity representative of the loading resistance of the unit is less than or equal to a permissible maximum value; and the or each substrate and the or each layer of interlayer are prepared and assembled to the adjusted dimensions.

6 Claims, 5 Drawing Sheets

(56) References Cited

U.S. PATENT DOCUMENTS

| | | |
|---|---|---|
| 6,432,522 B1 | 8/2002 | Friedman et al. |
| 8,683,871 B2 * | 4/2014 | Decourcelle et al. ........... 73/785 |
| 2002/0006504 A1 * | 1/2002 | Rehfeld et al. ................ 428/212 |
| 2008/0216940 A1 * | 9/2008 | van Peer et al. ................ 156/99 |
| 2011/0200831 A1 | 8/2011 | Decourcelle et al. |
| 2012/0034439 A1 | 2/2012 | Milamon et al. |
| 2013/0149931 A1 * | 6/2013 | Rukavina et al. ............. 442/135 |

* cited by examiner

PROCESS FOR MANUFACTURING A LAMINATED GLAZING UNIT

CROSS-REFERENCE TO RELATED APPLICATIONS

The present application is the U.S. counterpart of WO 2011/00862 and is based on and claims priority to French application no. FR 09 54466 filed Jun. 30, 2009, the entire contents of each of which are hereby incorporated herein by reference.

The present invention relates to a process for manufacturing a laminated glazing unit comprising at least one substrate having a glass function and at least one layer of polymeric interlayer. The invention also relates to an optimized laminated glazing unit.

In the context of the invention, the term "laminated glazing" is understood to mean any glazing structure comprising at least one substrate having a glass function and at least one layer of interlayer, including a structure comprising a single substrate and a single layer of interlayer joined together.

It is known that the laws describing the viscoelastic behavior of polymeric interlayers intended for the manufacture of laminated glazing units have an influence on the mechanical behavior of these units when they are subjected to a static or quasi-static load. To validate the design of a laminated glazing unit, it is necessary to check that its loading resistance is compatible with its application. For example, it is necessary to check that a glazing unit of a building facade is capable of withstanding a certain wind loading, or that a photovoltaic module intended to be installed on the roof of a building is capable of withstanding a certain snow loading. In particular, the intensity of a foreseeable load on a laminated glazing unit and the way in which said load is distributed on the laminated glazing unit, together with the characteristic time and characteristic temperature ranges of this load, are parameters to be considered when manufacturing the laminated glazing unit.

One conventional method of determining the loading resistance of a laminated glazing unit, under defined support and load conditions, consists in using an analytical model in which the laminated glazing unit is assimilated to a glazing unit with no interlayer and the participation of the interlayer to shear transfer in the laminated glazing unit is represented by a transfer coefficient $\bar{\omega}$ of between 0 and 1. The contribution of the interlayer to the mechanical performance of the laminated glazing unit is greater the higher the transfer coefficient $\bar{\omega}$. In practice, the transfer coefficient $\bar{\omega}$ is used to define an equivalent thickness of the laminated glazing unit, on the basis of which quantities representative of the loading resistance of the laminated glazing unit may be calculated, using formulae similar to those applicable to monolithic glazing units.

To give an example, in this conventional method, the equivalent thickness for calculating the deflection of a laminated glazing panel is given by the equation:

$$h_{ef;w} = \sqrt[3]{(1-\bar{\omega})\sum_i h_i^3 + \bar{\omega}\left(\sum_i h_i\right)^3}, \quad (I)$$

and the equivalent thickness for calculating the maximum stress on the substrate i having a glass function of a laminated glazing panel is given by the equation:

$$h_{ef;\sigma;i} = \sqrt{\frac{(h_{ef;w})^3}{(h_i + 2\bar{\omega}h_{m;i})}}, \quad (II)$$

in which $h_i$ is the thickness of the or each substrate having a glass function of the laminated glazing panel, and $h_{m;i}$ is the distance between the mean plane of the substrate i having a glass function and the mean plane of the laminated glazing unit without taking into account the thicknesses of the layers of interlayer used in the laminated glazing unit.

However, no method for precisely determining the transfer coefficient $\bar{\omega}$ for a given laminated glazing unit is available in the literature. In addition, in the conventional method, the equivalent thickness is expressed as a function of the transfer coefficient $\bar{\omega}$ of the interlayer and the thickness of the or each substrate of the laminated glazing unit, without taking into account the interlayer thickness in the laminated glazing unit. Now, in cases in which the contribution to the mechanical performance of the laminated glazing unit by the interlayer cannot be neglected, the absence of dependency of the equivalent thickness with respect to the interlayer thickness may lead to an overapproximation of the mechanical behavior of the structure. In particular, in the conventional method, no distinction is made between a laminated glazing unit having a single interlayer ply of standard thickness, placed between two glass substrates, and a laminated glazing unit comprising two plies of standard thickness of the same interlayer, which are placed between the same two glass substrates. As a result, when establishing the specifications for the design of a laminated glazing unit, there is a tendency to overestimate the necessary thicknesses of the glass substrates, while an increase in the interlayer thickness could be sufficient for satisfying the design criteria. Consequently, the cost and the weight of the laminated glazing units obtained within the context of the conventional method are not optimized.

It is these drawbacks that the invention is more particularly aimed at remedying, by providing a process for manufacturing a laminated glazing unit that guarantees that the laminated glazing unit obtained is optimized both in terms of weight and of loading resistance.

For this purpose, one subject of the invention is a process for manufacturing a laminated glazing unit so that it withstands a predetermined load corresponding to a characteristic time range and to a characteristic temperature range, the laminated glazing unit comprising at least one substrate having a glass function and at least one layer of polymeric interlayer, characterized in that it comprises steps in which:

the law describing the viscoelastic behavior of the constituent material of the interlayer over the characteristic time and characteristic temperature ranges of the predetermined load is obtained;

the maximum value of at least one quantity representative of the loading resistance of the laminated glazing unit subjected to the predetermined load is calculated, using—an analytical model in which the contribution of the interlayer to shear transfer in the laminated glazing unit is represented by a transfer coefficient, and—an equation expressing the transfer coefficient as a function of the Young's modulus of the interlayer, of the applied load on the laminated glazing unit and of the dimensions of the laminated glazing unit;

the dimensions of the laminated glazing unit are adjusted in such a way that the calculated maximum value of the quantity representative of the loading resistance of the laminated glazing unit is less than or equal to a permissible maximum value;

the substrate and the layer of interlayer of the laminated glazing unit are prepared and assembled to the adjusted dimensions.

In the context of the invention, the expression "dimensions of the laminated glazing unit" is understood to mean not only its peripheral dimensions, for example in the case of a rectangular laminated glazing panel, its width and its length, but also the thicknesses of its substrate or substrates and that of its constituent layer or layers of interlayer.

According to other advantageous features of a process for manufacturing a laminated glazing unit according to the invention, taken in isolation or in any technically possible combination:

In order to determine the behavior law of the constituent material of the interlayer, the Young's modulus is measured on a sample of the interlayer using a viscoanalyzer, by varying the frequency and the temperature while imposing a constant dynamic displacement, and the law of frequency/temperature equivalence established by the WLF method is used.

The behavior law of the constituent material of the interlayer is determined over a frequency range between $5 \times 10^{-7}$ Hz and $3 \times 10^{-1}$ Hz and a temperature range between $-20°$ C. and $60°$ C.

The following are calculated as quantities representative of the loading resistance of the laminated glazing unit:

the deflection of the laminated glazing unit, on the basis of the equivalent thickness $h_{ef;w}$ of the laminated glazing such that:

$$h_{ef;w} = \sqrt[3]{(1-\varpi)\left(\sum_i h_i^3 + \sum_j h_{int_j}^3\right) + \varpi\left(\sum_i h_i + \sum_j h_{int_j}\right)^3}, \quad \text{(III)}$$

and/or the maximum stress on the or each substrate having a glass function of the laminated glazing unit, on the basis of the equivalent thickness $h_{ef;\sigma;i}$ of the laminated glazing, such that:

$$h_{ef;\sigma;i} = \sqrt{\frac{(h_{ef;w})^3}{(h_i + 2\varpi h_{m;i})}}, \quad \text{(IV)}$$

in which $h_i$ is the thickness of the or each substrate having a glass function;

$h_{int_j}$ is the thickness of the or each layer of interlayer;

$h_{m;i}$ is the distance between the mean plane of the substrate i having a glass function and the mean plane of the laminated glazing unit.

The equation expressing the transfer coefficient, valid for any laminated glazing unit comprising at least one substrate having a glass function and at least one layer of polymeric interlayer, is determined according to the following steps:

the law describing the viscoelastic behavior of the constituent material of the interlayer of the laminated glazing unit is obtained;

a finite-element numerical model in bending of the laminated glazing unit is established, using the behavior law of the constituent material of the interlayer to define the mechanical properties of the interlayer;

a comparison is made between the results obtained, on the one hand, with the numerical model and, on the other hand, with an analytical model in which the contribution of the interlayer to shear transfer is represented by a transfer coefficient, and the value of the transfer coefficient is adjusted until convergence of these results;

a transfer function representative of the variation of the transfer coefficient as a function of the Young's modulus of the interlayer is constructed by successive iterations;

the transfer function is put in equation form in such a way that the transfer coefficient is expressed as a function of the Young's modulus of the interlayer, of the applied load on the laminated glazing unit and of the dimensions of the laminated glazing unit;

the parameters of the equation expressing the transfer coefficient as a function of the Young's modulus of the interlayer, of the applied load on the laminated glazing unit and of the dimensions of the laminated glazing unit are determined empirically.

The laminated glazing unit is a rectangular panel, the dimensions of the laminated glazing unit in the equation expressing the transfer coefficient being the width and the length of the panel, the thickness of the or each substrate having a glass function and the thickness of the or each layer of interlayer.

Another subject of the invention is a data recording medium comprising instructions for implementing the calculation steps of a manufacturing process as described above, when these instructions are executed by an electronic computing unit, said instructions including an instruction to calculate the maximum value of at least one quantity representative of the loading resistance of the laminated glazing unit subjected to the predetermined load, using—an analytical model in which the contribution of the interlayer to shear transfer in the laminated glazing unit is represented by a transfer coefficient, and—an equation expressing the transfer coefficient as a function of the Young's modulus of the interlayer, of the applied load on the laminated glazing unit and of the dimensions of the laminated glazing unit.

According to one embodiment, the instructions include, after the instruction to calculate the maximum value of at least one quantity representative of the loading resistance of the laminated glazing unit subjected to said predetermined load, an instruction to calculate adjusted values of the dimensions of the laminated glazing unit in such a way that the calculated maximum value of the representative quantity is less than or equal to a permissible maximum value of this representative quantity.

Another subject of the invention is a laminated glazing unit obtained by a manufacturing process as described above.

Another subject of the invention is a laminated glazing unit intended to be installed on a site corresponding to a predetermined maximum load applied on the unit, this laminated glazing unit comprising at least one substrate having a glass function and at least one layer of polymeric interlayer, this laminated glazing unit having an interlayer thickness and/or a substrate thickness that are lower than, respectively, the interlayer thickness and the substrate thickness of a corresponding nominal laminated glazing unit, the other dimensions of the laminated glazing unit being kept equal to those of the corresponding nominal laminated glazing unit, in which the corresponding nominal laminated glazing unit is a laminated glazing unit manufactured for resisting said predetermined maximum load by a manufacturing method in which the equivalent thickness of the laminated glazing unit, on the basis of which the representative quantities of the loading resistance of the unit are calculated using formulae similar to those applicable to monolithic glazing units, is independent of the thickness of the layer of interlayer.

According to other advantageous features of a laminated glazing unit according to the invention:

The laminated glazing unit is a glazing unit of a building comprising at least two substrates having a glass function and at least one layer of polymeric interlayer, the or each layer of interlayer being placed between two substrates having a glass function.

The laminated glazing unit is a photovoltaic module comprising a front substrate having a glass function and at least one photovoltaic cell, a layer of polymeric lamination interlayer being inserted between the front substrate and the photovoltaic cell.

The features and advantages of the invention will become apparent in the following description of several embodiments of a manufacturing process and of a laminated glazing unit according to the invention, given solely by way of example and with reference to the appended drawings in which.

Figure 2:
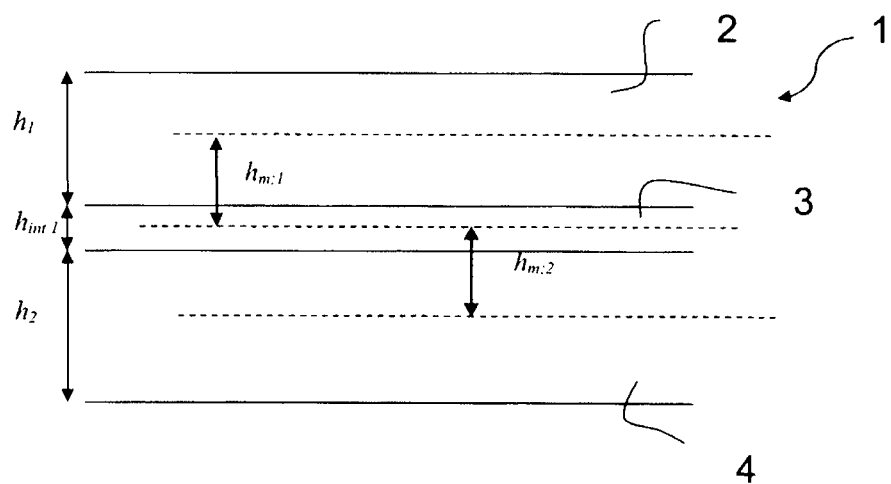
FIG. 2 is a partial section along plane II of FIG. 1.
Figure 10:
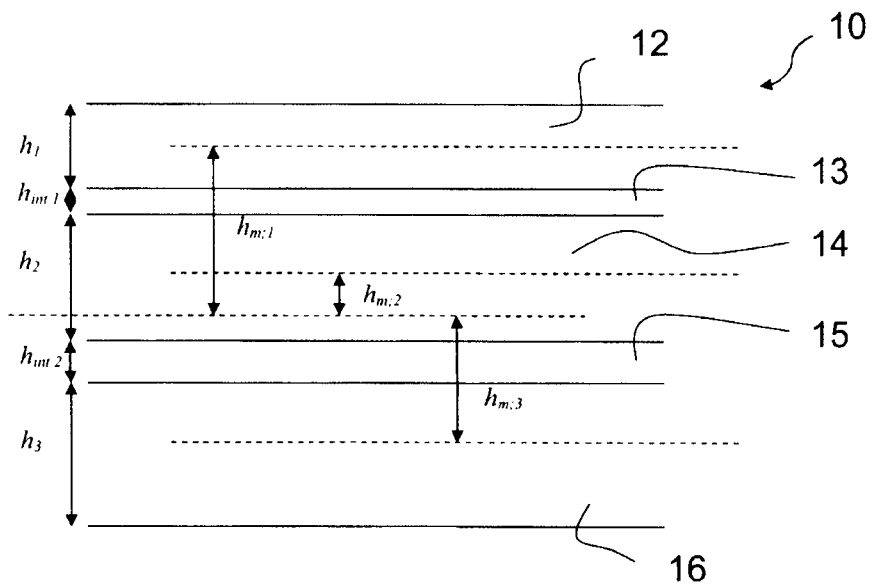
Figure 4:
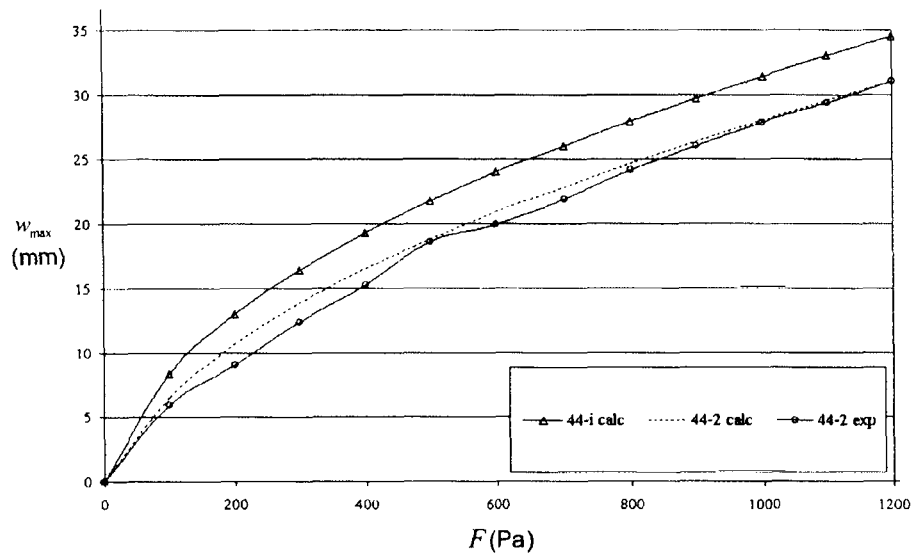
Figure 5:
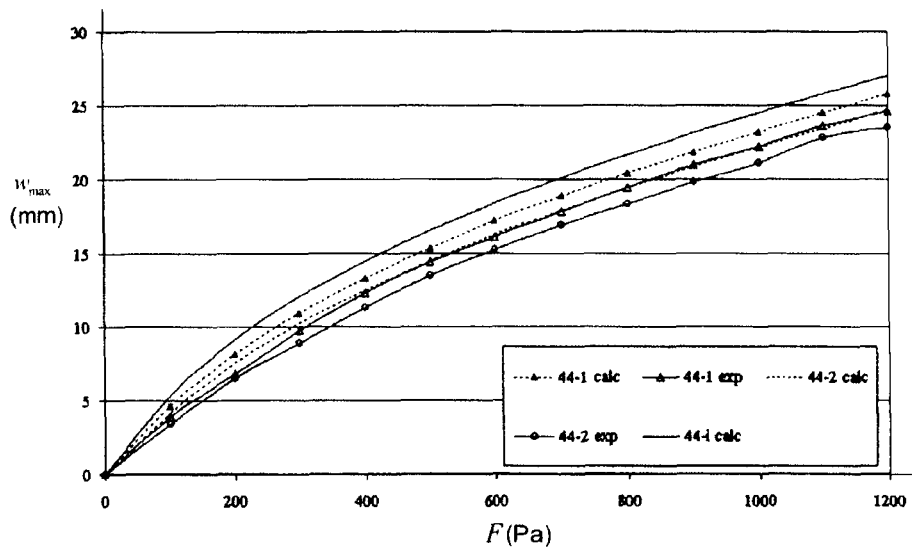
Figure 6:
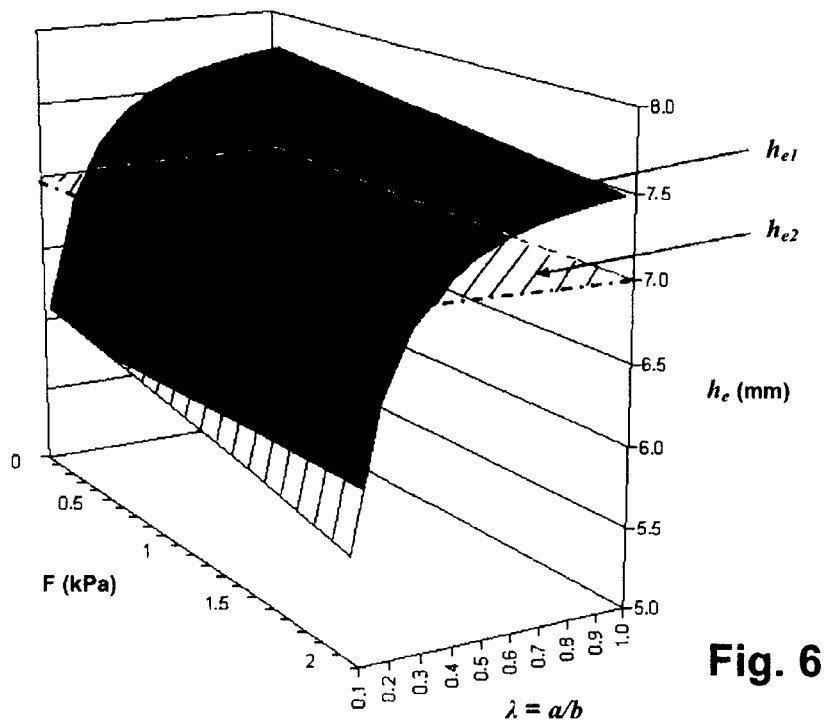
Figure 7:
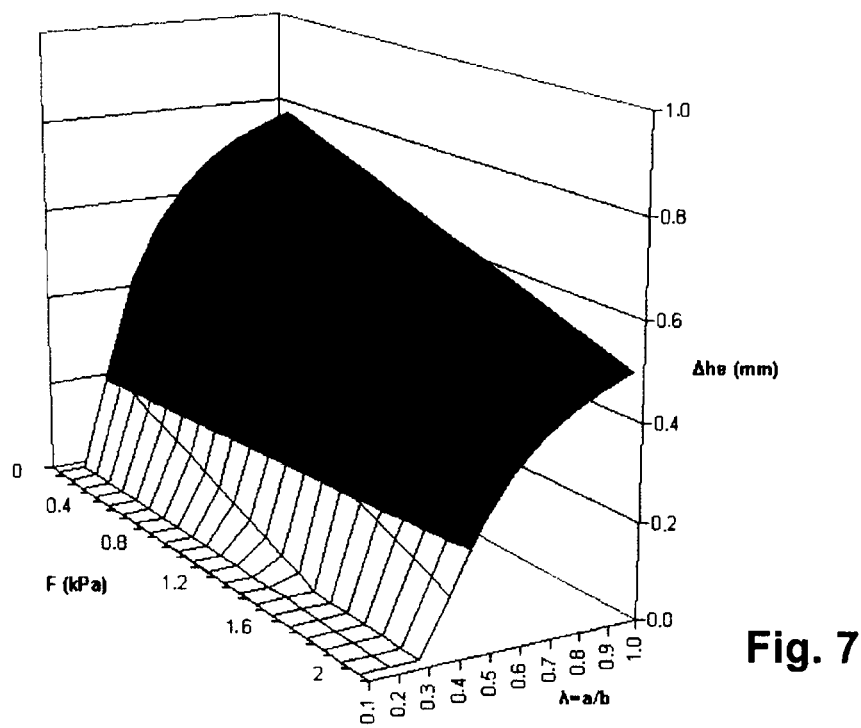
Figure 8:
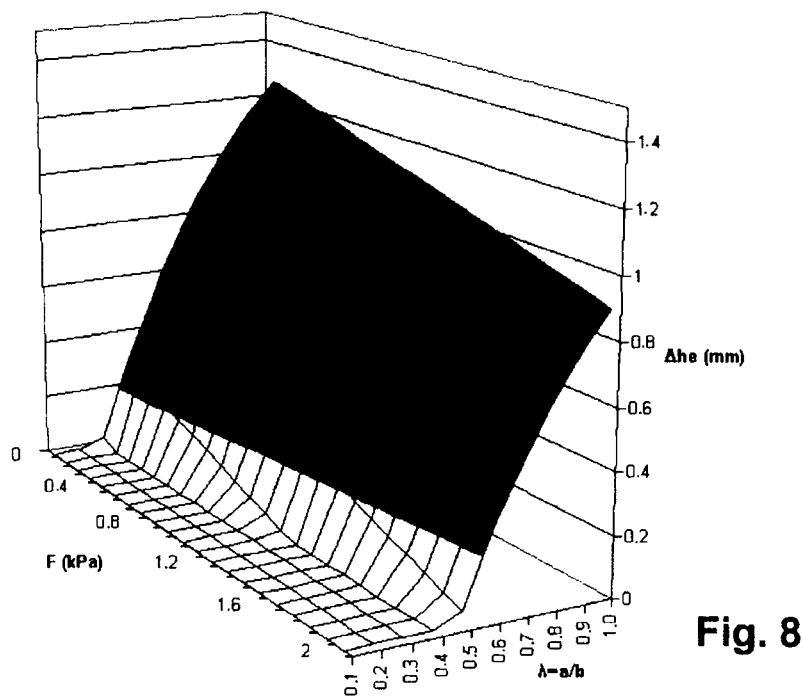
Figure 9:
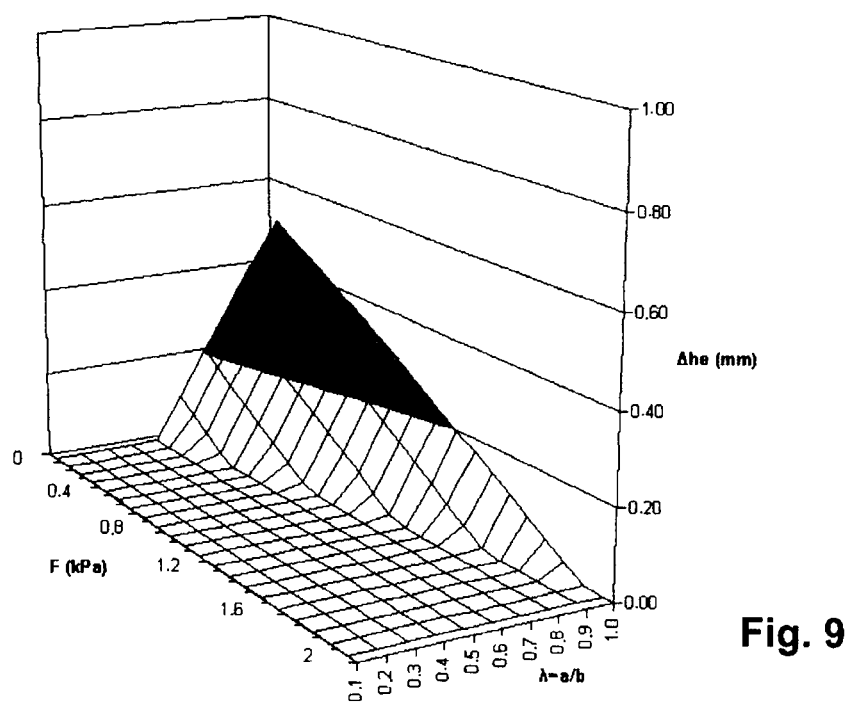

FIG. 4 is a graph showing the variation of the maximum deflection of a rectangular laminated glazing panel as a function of the wind loading applied to the panel, obtained respectively by an experimental measurement, by estimation in the context of a process for manufacturing a laminated glazing unit of the prior art and by estimation in the context of the process for manufacturing a laminated glazing unit according to the invention, for a panel having a width of 2 m and a length of 3 m and comprising two glass substrates, each having a thickness of 4 mm, and two standard interlayer plies, i.e. a layer of interlayer having a thickness of 0.76 mm;

FIG. 5 is a graph showing the variation of the maximum deflection of a rectangular laminated glazing panel as a function of the wind loading applied to the panel, obtained respectively by an experimental measurement, by estimation in the context of a process for manufacturing a laminated glazing unit of the prior art and by estimation in the context of the process for manufacturing a laminated glazing unit according to the invention, for a panel having a width of 2 m and a length of 3 m and comprising two glass substrates, each having a thickness of 4 mm, and one or two structural interlayer plies, i.e. a layer of interlayer having a thickness of 0.38 mm or 0.76 mm;

FIG. 6 is a three-dimensional graph representative of the equivalent thickness of a rectangular laminated glazing panel as a function both of the applied wind loading on the panel and the width/length ratio $\lambda=a/b$ of the panel, for a panel having a length of 3 m and comprising two glass substrates, each having a thickness of 4 mm, and two structural interlayer plies, i.e. a layer of interlayer having a thickness of 0.76 mm, respectively for a laminated glass panel according to the invention and for a corresponding nominal laminated glazing panel of the prior art;

FIG. 7 is a three-dimensional graph derived from FIG. 6, representative of the saving in terms of equivalent thickness of the laminated glazing panel according to the invention shown in FIG. 6, compared to the equivalent thickness of a corresponding nominal laminated glazing panel of the prior art, as a function both of the wind loading applied on the panel and the width/length ratio $\lambda=a/b$ of the panel;

FIG. 8 is a graph similar to the graph shown in FIG. 7, representative of the saving in terms of equivalent thickness of a rectangular laminated glazing panel as a function both of the applied wind loading on the panel and the width/length ratio $\lambda=a/b$ of the panel, for a panel having a length of 3 m and comprising two glass substrates, each having a thickness of 4 mm, and two standard interlayer plies, i.e. a layer of interlayer having a thickness of 0.76 mm, respectively for a laminated glazing panel according to the invention and for a corresponding nominal laminated glazing panel of the prior art;

FIG. 9 is a graph similar to the graph shown in FIG. 7, representative of the saving in terms of equivalent thickness of a rectangular laminated glazing panel as a function both of the applied wind loading on the panel and the width/length ratio $\lambda=a/b$ of the panel, for a panel having a length of 3 m and comprising two glass substrates, each having a thickness of 4 mm, and two acoustic interlayer plies, i.e. a layer of interlayer having a thickness of 0.76 mm, respectively for a laminated glazing panel according to the invention and for a corresponding nominal laminated glazing panel of the prior art; and FIG. 10 is a section similar to FIG. 2 for a laminated glazing panel comprising three substrates having a glass function and two layers of polymeric interlayer each placed between two substrates.

Figure 1:
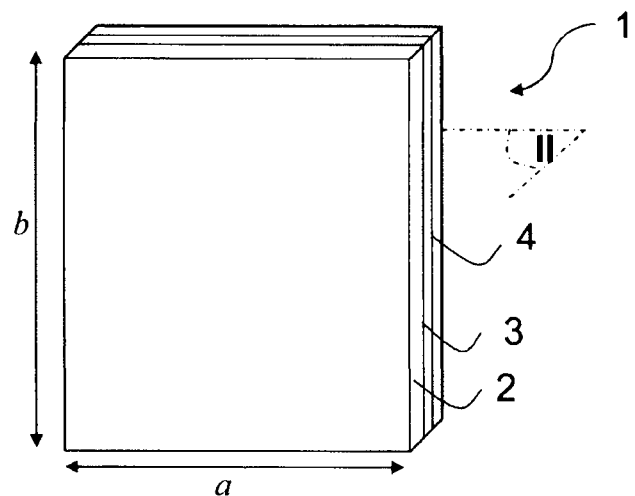
FIG. 1 is a schematic perspective view of a laminated glazing panel comprising two substrates having a glass function and a polymeric interlayer.

FIG. 1 shows a laminated glazing panel 1 of rectangular shape, comprising two glass substrates 2 and 4 between which is bonded a layer 3 of interlayer based on polyvinyl butyral (PVB). As a variant, the layer 3 of interlayer may be made of any viscoelastic material of suitable properties other than PVB. The width and the length of the panel 1 are denoted a and b, respectively, the thicknesses of the substrates 2 and 4 are denoted $h_1$ and $h_2$, and the thickness of the layer 3 of interlayer is denoted $h_{int1}$. An aim of the manufacturing process according to the invention is to design the laminated glazing panel 1 so that it withstands a predetermined load $F_0$, such as a snow loading in the first embodiment, or a wind loading in the second embodiment illustrated in FIGS. 4 to 9.

A prior step, key for implementing the manufacturing process according to the invention, is to determine an equation expressing the transfer coefficient $\overline{\omega}$ of the interlayer of a laminated glazing panel as a function of the Young's modulus $E_{int}$ of the interlayer, the applied load F on the panel and the dimensions a, b, $h_i$, $h_{intj}$ of the laminated glazing panel. This equation, valid for any laminated glazing panel comprising at least one substrate having a glass function and at least one layer of polymeric interlayer, is determined according to the steps described below.

Firstly, the law describing the viscoelastic behavior $E_{int}$ (t, T) of the constituent material of the interlayer of the laminated glazing panel is determined experimentally. The variation of the Young's modulus $E_{int}$ as a function of the frequency and the temperature is determined for a frequency (f=1/t) range of between $5\times10^{-7}$ Hz and $3\times10^{-1}$ Hz and a temperature (T) range of between $-20°$ C. and $60°$ C. These frequency and temperature ranges correspond to the characteristic ranges for static or quasi-static loads applied on laminated glazing units, for example when they are fitted into buildings. In particular, the characteristic time t of a wind loading is around 3 seconds, with a corresponding temperature (T) range of between $0°$ C. and $20°$ C., whereas the characteristic time t of a snow loading is around 3 weeks, with a corresponding temperature (T) range of between $-20°$ C. and $20°$ C.

To determine the behavior law $E_{int}$ (t, T), the Young's modulus $E_{int}$ is measured on a sample of the interlayer using a viscoanalyzer, for example Metravib VA400 viscoanalyzer, by varying the frequency and the temperature, while imposing a constant dynamic displacement. To give an example, the dynamic displacement is fixed at $1 \times 10^{-6}$ m. The Metravib viscoanalyzer provides values only for the 1 to 400 Hz frequency range. For frequency and temperature values for which it is not possible to take a measurement using the viscoanalyzer, the frequency/temperature equivalence law established by the WLF (Williams-Landel-Ferry) method is used in a known manner.

A finite-element numerical model in bending of the laminated glazing panel is then established so as to calculate the loading resistance of the laminated glazing panel subjected to a certain load. The mechanical properties of the interlayer are defined, for this numerical model, using the behavior law $E_{int}$ (t, T) determined beforehand. To give an example, this numerical model may be established using COSMOS-M calculation software, into which a nonlinear model of a laminated glazing panel incorporating the interlayer is integrated, with simple supports on each of the four sides of the panel and a uniform load.

The results of the numerical calculation are then compared with those obtained by analytical formulae in which the contribution of the interlayer to shear transfer in the laminated glazing panel is represented by the transfer coefficient $\bar{\omega}$. These analytical formulae may for example allow the maximum deflection $w_{max}$ of the laminated glazing panel and the maximum stress $\sigma_{max}^i$ on the substrate i having a glass function of the laminated glazing panel to be calculated as follows:

$$w_{max} = k_4 \frac{A^2}{h_{ef;w}^3} \frac{F}{E_{int}} \quad (V)$$

and $$\sigma_{max}^i = k_1 \frac{A}{h_{ef;\sigma;i}^2} F \quad (VI)$$

in which $h_{ef;w}$ is the equivalent thickness for calculating the maximum deflection $w_{max}$, as defined in the aforementioned expression (I); $h_{ef;\sigma;i}$ is the equivalent thickness for calculating the maximum stress $\sigma_{max}^i$, as defined in the aforementioned expression (II); F is the applied load on the laminated glazing panel; $E_{int}$ is the Young's modulus of the interlayer of the laminated glazing panel; A is equal to the product ab of the width a and the length b of the laminated glazing panel; $k_1$ and $k_4$ are coefficients having the values given in Annex B of the draft European Standard prEN 13474.

As a variant, in order to take into account the interlayer thickness in the laminated glazing panel, it is possible to reformulate the expressions of the equivalent thickness, for calculating the maximum deflection and the maximum stress according to formulae (V) and (VI), in the following manner:

$$h_{ef;w} = \sqrt[3]{(1-\varpi)\left(\sum_i h_i^3 + \sum_j h_{int_j}^3\right) + \varpi\left(\sum_i h_i + \sum_j h_{int_j}\right)^3}, \quad (III)$$

$$h_{ef;\sigma;i} = \sqrt{\frac{(h_{ef;w})^3}{(h_i + 2\varpi h_{m;i})}}, \quad (IV)$$

in which $h_i$ is the thickness of the or each substrate having a glass function of the laminated glazing panel;

$h_{int_j}$ is the thickness of the or each layer of interlayer of the laminated glazing panel;

$h_{m;i}$ is the distance between the mean plane of the substrate i having a glass function and the mean plane of the laminated glazing panel, taking into account the thicknesses of the layers of interlayer used in the laminated glazing unit, as shown in FIGS. 1 and 10.

By comparing the results obtained from the numerical model, on the one hand, and those obtained from the analytical formulae, on the other hand, the value of the transfer coefficient $\bar{\omega}$ is adjusted so as to make the results converge. Thus, a transfer function representative of the variation of the transfer coefficient $\bar{\omega}$ as a function of the Young's modulus $E_{int}$ of the interlayer is constructed by successive iterations. The curve representative of such a transfer function $\bar{\omega}=f(E_{int})$ is shown in FIG. 3.

The transfer function is then put in equation form using an empirical formula so as to express the transfer coefficient $\bar{\omega}$ as a function not only of the properties of the interlayer, but also of the applied load F on the panel and of physical parameters of the laminated glazing panel. This step of putting the transfer function in equation form constitutes a key step of the invention, the equation of the transfer coefficient $\bar{\omega}$ then being able to be used systematically so as to obtain a laminated glazing unit optimized in terms of weight and loading resistance.

Figure 3:
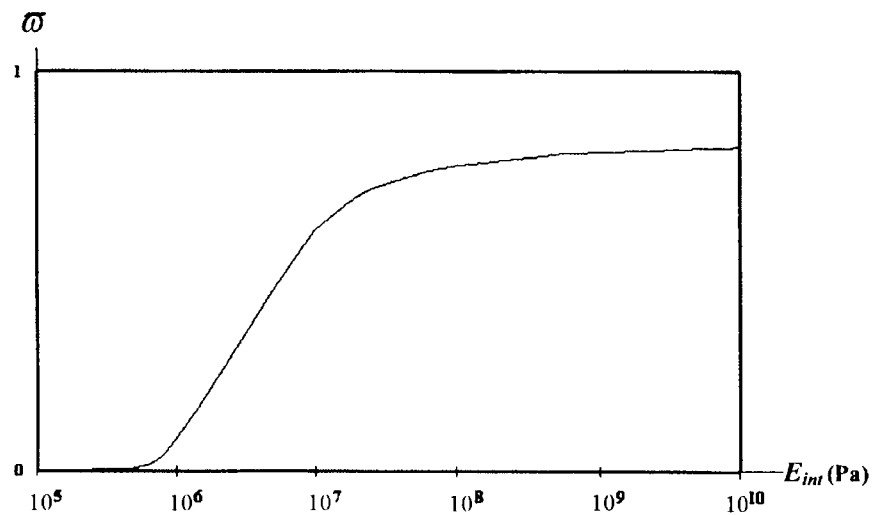
FIG. 3 is a curve representative of the variation of the transfer coefficient as a function of the Young's modulus of the interlayer.

From the curve representative of the transfer function obtained above, an example of which is shown in FIG. 3, it has been found that the characteristic equation for the transfer function $\bar{\omega}=f(E)$ is of the following form:

$$\varpi = \frac{1}{\alpha + \frac{\beta}{G}},$$

in which $\alpha$ is a constant;

$\beta$ is a group of physical and geometric parameters of the panel; and

G is the shear modulus of the interlayer, which can be determined from the Poisson's ratio $\nu$ and the Young's modulus $E_{int}$ of the interlayer using the equation $E_{int}=2(1+\nu)G$.

The inventors have determined empirically the parameters of the transfer function equation on the basis of experimental results obtained from measuring the maximum deflections of laminated glazing panels, during wind trials, and also on the basis of numerical calculation results obtained from a finite-element model in bending of laminated glazing panels. More precisely, the inventors have studied the sensitivity of the transfer coefficient $\bar{\omega}$ with respect to several parameters. To a first approximation, the transfer coefficient $\bar{\omega}$ depends on the width a and the length b of the panel, on the thickness $h_i$ of the or each glass substrate of the laminated glazing panel, on the thickness $h_{int_j}$ of the or each layer of interlayer of the laminated glazing panel, on the uniformly distributed load F applied on the panel, on the Young's modulus $E_v$ (70 GPa) of the glass and on the Young's modulus $E_{int}$ of the interlayer.

It has been found that the transfer coefficient $\bar{\omega}$ varies linearly as a function of the applied load on the laminated glazing panel, irrespective of the thickness and the type of interlayer used. This is because the intensity of the loading governs the deformation energy in bending of the assembly and thus, in a certain manner, the shear forces transmitted from one glass substrate of the laminated glazing panel to another. The more the laminated glazing panel deforms under the loading, the more stress on the interlayer and the lower its transfer capability. This results in the following affine expression as a function of the applied load F on the laminated glazing panel:

$$\varpi = \varphi F + \frac{1}{\alpha + \frac{\beta}{G}},$$

in which the value of the slope $\varphi$ is set at $-5e^{-5}$ by interpolating the experimental and numerical data of laminated glazing panels in bending. The ratio $$\frac{1}{\alpha + \frac{\beta}{G}}$$

then becomes the intercept on the y-axis, which determines the potential stiffness of the assembly under no external action.

These considerations result in the following expression for the transfer coefficient $\overline{\omega}$ of a laminated glazing panel comprising at least one substrate having a glass function and at least one layer of polymeric interlayer:

$$\varpi = -5e^{-5}F + \frac{1}{1.3 + \frac{0.6 E_v \sum h_{int_j} \sum h_i}{\sqrt{ab}\, E_{int} h_{tot} \lambda}}, \quad \text{(VII)}$$

in which $\lambda$ is the ratio $a/b$, $h_{tot}$ is the total thickness of the laminated glazing panel, where i varies from 1 to n and j varies from 1 to n−1, n representing the number of substrates having a glass function of the laminated glazing panel.

This equation (VII) expressing the transfer coefficient $\overline{\omega}$ of a laminated glazing panel is used in the context of the manufacturing process according to the invention in the manner described hereinafter and illustrated, by way of example, in the first and second embodiments below.

When it is desired to manufacture a laminated glazing panel, for example the laminated glazing panel 1 of FIG. 1, so that it withstands a predetermined load $F_0$ corresponding to a characteristic time (t) range and to a characteristic temperature (T) range, the law describing the viscoelastic behavior $E_{int}(t, T)$ of the constituent material of the interlayer is firstly determined, by covering at least the characteristic time and temperature ranges of the load $F_0$. The behavior law $E_{int}(t, T)$ is determined as described above, using a viscoanalyzer, by varying the frequency and the temperature and by imposing a constant dynamic displacement, and, for frequencies and temperatures for which it is not possible to take a measurement using the viscoanalyzer, by using the frequency/temperature equivalence law established by the WLF (Williams-Landel-Ferry) method. In practice, the behavior law $E_{int}(t, T)$ is determined just once for each interlayer composition and stored in memory in a database where it can be used again in the process for manufacturing any laminated glazing panel incorporating this interlayer composition.

The maximum value of at least one quantity representative of the loading resistance of the laminated glazing panel subjected to the predetermined load $F_0$, such as the maximum deflection $w_{max}$ of the laminated glazing panel and/or the maximum stress $\sigma_{max}^i$ on the or each substrate having a glass function of the panel, is then calculated. For this purpose, the equation (VII) expressing the transfer coefficient $\overline{\omega}$ of the laminated glazing panel is used in combination with analytical formulae, for example formulae (V) and (VI) for calculating the maximum deflection and the maximum stress and formulae (III) and (IV) for the equivalent thickness taking the interlayer thickness in the laminated glazing panel into account.

The dimensions a, b, $h_i$, $h_{int_j}$ of the laminated glazing panel are then adjusted in such a way that the calculated maximum value of the or each quantity $w_{max}$, $\sigma_{max}^i$ representative of the loading resistance of the laminated glazing panel is less than or equal to a permissible maximum value defined, for example, by a standard. The maximum value of the or each calculated quantity $w_{max}$, $\sigma_{max}^i$ is the maximum value over the characteristic time and characteristic temperature ranges of the load $F_0$. In practice, the maximum value of the calculated maximum stress $\sigma_{max}^i$ is the maximum value over the characteristic time range of the load $F_0$ since the maximum stress is not influenced by the temperature over the temperature ranges in question.

Once the adjusted dimensions a, b, $h_i$, $h_{int_j}$ have been determined, the or each substrate and the or each layer of interlayer of the laminated glazing panel are prepared with the adjusted thicknesses $h_i$, $h_{int_j}$, and are assembled so as to form the laminated glazing panel with likewise adjusted width a and length b.

The calculation steps described above for the manufacturing process according to the invention may be carried out by means of a computing unit programmed with an input data processing algorithm, in which the algorithm involves equation (VII) expressing the transfer coefficient $\overline{\omega}$, together with analytical formulae for calculating the loading resistance of a laminated glazing panel, especially formulae (V) and (VI) for calculating the maximum deflection and the maximum stress, and formulae (III) and (IV) for the equivalent thickness. The computing unit is based on a conventional programmable computing unit capable of executing instructions recorded on a data recording medium. This medium includes instructions for executing the algorithm described above when these instructions, which correspond to the calculation steps of the manufacturing process according to the invention, are carried out by the computing unit. The set of instructions for executing the algorithm are integrated into a laminated glazing design program or software, which advantageously includes a simplified graphical interface enabling a user to solve a design problem rapidly and reliably.

In a first approach, the input data for the algorithm may be the behavior law $E_{int}(t, T)$ of the interlayer of the laminated glazing panel, the predetermined load $F_0$ applied on the laminated glazing panel and the dimensions a, b, $h_i$, $h_{int_j}$ of the panel. The computing unit is then designed to deliver, as output, the calculated values of quantities representative of the loading resistance of the laminated glazing panel in question, in particular the maximum deflection of the panel and/or the maximum stress on each glass substrate i of the unit. This first approach makes it possible to check whether a laminated glazing panel of given dimensions is correctly designed for a particular application. With this first approach, it is also possible, by modifying, step by step, the dimensions a, b, $h_i$, $h_{int_j}$ of the panel supplied as input data for the algorithm, to adjust the dimensions of the panel iteratively in such a way that the calculated maximum value of the or each quantity $w_{max}$, $\sigma_{max}^i$ representative of the loading resistance of the laminated glazing panel is less than or equal to a corresponding permissible maximum value, this permissible maximum value being for example defined by a standard.

In a second approach, for the purpose of directly optimizing the design of the laminated glazing panel, the input data for the algorithm may be the behavior law $E_{int}(t, T)$ of the interlayer of the laminated glazing panel, the predetermined load $F_0$ applied on the laminated glazing panel, the permissible maximum value of one or more quantities representative of the loading resistance of the laminated glazing panel, in particular the maximum deflection of the panel and/or the maximum stress on each glass substrate i of the unit, and some of the dimensions a, b, $h_i$ or $h_{intj}$ of the laminated glazing panel. The permissible maximum values of quantities representative of the loading resistance of the laminated glazing panel are for example defined by a standard. The computing unit is then designed to deliver, as output, adjusted values of the other dimensions a, b, $h_i$ or $h_{intj}$ of the laminated glazing panel that have not been supplied as input data for the algorithm, these adjusted values being adapted in such a way that the calculated maximum value of the or each quantity $w_{max}$, $\sigma_{max}^i$ representative of the loading resistance of the laminated glazing panel is less than or equal to the corresponding permissible maximum value supplied as input.

In a first example embodiment of the manufacturing process according to the invention, the aim is to design the laminated glazing panel 1 shown in FIG. 1. The panel 1 is intended to be positioned horizontally on the roof of a building and to be exposed to a snow loading of 650 Pa. In this example, the panel 1 has a width a and a length b of 1.5 m and the two glass substrates 2 and 4 have respective thicknesses $h_1$ of 6 mm and $h_2$ of 4 mm. The layer 3 of interlayer is a layer of what is called a structural interlayer and the aim is to determine the thickness $h_{int1}$ of this layer of interlayer so as to satisfy permissibility criteria in terms of loading resistance of the panel 1.

In this type of application, it is the maximum stress $\sigma_{max} i$ in the glass substrates 2 and 4 which is of more particular interest, because it is the most limiting criterion taking into account the static fatigue of a glass under a loading applied for a long period of time, which is the case of a snow loading.

Table 1 below shows the results obtained by calculation in the context of the conventional method for determining the loading resistance of a laminated glazing unit without taking into account the interlayer thickness. The considered value of the transfer coefficient $\overline{\omega}$ is the approximate value proposed in the draft European Standard prEN 13474 for structural interlayers and for a snow loading.

TABLE 1

|  | Ultimate limiting state | Service limiting state |
| --- | --- | --- |
| Loading Prescriptive criterion | 1127 Pa Maximum permissible stress for glass: 10.1 MPa | 885 Pa Permissible deflection of the panel: 15 mm |
| Result | Calculated stress for 6 mm: 11.2 MPa Calculated stress for 4 mm: 8.5 MPa | Calculated deflection: 6.5 mm |

It is apparent from Table 1 that the stress in the glass substrate 2 having a thickness of 6 mm exceeds the permissible criterion, whatever the thickness of the interlayer, since, in the conventional method, the thickness of the interlayer is not taken into account when formulating the equivalent thickness. Thus, with the conventional method, it appears to be necessary to increase the glass thickness in the laminated glazing panel so that it meets the permissibility criteria in terms of loading resistance.

Table 2 below gives the results obtained by calculation in the context of the manufacturing process according to the invention, for a laminated glazing panel 1 comprising two glass substrates 2 and 4 having respective thicknesses $h_1$ of 6 mm and $h_2$ of 4 mm and a layer 3 of structural interlayer having a thickness $h_{intj}$ of 0.76 mm bonded to the substrates 2 and 4. The panel is therefore a panel of the "64-2" type, as it comprises two glass substrates of 6 mm and 4 mm thickness respectively and two interlayer plies.

TABLE 2

|  | Ultimate limiting state | Service limiting state |
| --- | --- | --- |
| Loading Criterion | 1127 Pa Maximum permissible stress for glass: 10.1 MPa | 885 Pa Permissible deflection of the panel: 15 mm |
| Result | Calculated stress for 6 mm: 9.5 MPa Calculated stress for 4 mm: 7.4 MPa | Calculated deflection: 5.6 mm |

As Table 2 shows, taking the interlayer thickness in the laminated glazing panel into account and calculating the transfer coefficient $\overline{\omega}$ according to equation (VII) result in a design that meets the permissibility criteria.

It is apparent from this first embodiment that taking the interlayer thickness into account in designing the laminated glazing units, as intended within the context of the manufacturing process according to the invention, makes it possible to provide a thinner glass composition of the laminated glazing unit meeting the permissibility criteria in terms of loading resistance.

In the second embodiment illustrated in particular in FIGS. 4 and 5, the aim is to confirm the mechanical strength of the laminated glazing panel 1 shown in FIG. 1, having a width a of 2 m and a length b of 3 m, subjected to a wind loading of between 0 and 1200 Pa. Each of the two glass substrates 2 and 4 of the panel 1 has a thickness $h_1$, $h_2$ of 4 mm.

FIG. 4 shows the variation of the maximum deflection $w_{max}$ of the panel 1 as a function of the applied wind loading on the panel, when the panel 1 comprises a layer 3 of standard interlayer having a thickness $h_{int1}$ of 0.76 mm bonded to the glass substrates 2 and 4. The panel 1 is then a panel of the "44-2" type, since it comprises two glass substrates each of 4 mm thickness and two interlayer plies. FIG. 4 shows the results obtained by an experimental measurement (44-2 exp), by calculation in the context of the conventional method for determining the loading resistance of a laminated glazing unit without taking into account the interlayer thickness in the laminated glazing unit (44-i calc) and by calculation in the context of the manufacturing process according to the invention (44-2 calc), respectively.

FIG. 5 shows the variation of the maximum deflection $w_{max}$ of the panel 1 as a function of the applied wind loading on the panel, when the panel 1 comprises a layer 3 of structural interlayer bonded to the glass substrates 2 and 4 each of 4 mm thickness, the layer 3 having a thickness $h_{int1}$ either of 0.38 mm, corresponding to one interlayer ply, or of 0.76 mm, corresponding to two interlayer plies. In the first case the panel 1 is of the "44-1" type, and in the second case it is of the "44-2" type, as previously. FIG. 5 shows the results obtained by an experimental measurement (44-1 exp, 44-2 exp), by calculation in the context of the conventional method for determining the loading resistance of a laminated glazing unit without taking into account the interlayer thickness in the laminated glazing unit (44-i calc) and by calculation in the context of the manufacturing process according to the invention (44-1 calc, 44-2 calc), respectively.

By comparing the results shown in FIGS. 4 and 5, it is apparent that the maximum deflection predictions are more precise in the context of the manufacturing process according to the invention, thanks to taking the interlayer thickness in the laminated glazing panel into account. The examples in FIGS. 4 and 5 thus illustrate the added value of the process according to the invention, which results in better evaluation of the mechanical role of the interlayer.

Again in the context of this second embodiment, FIG. 6 shows a three-dimensional graph representative of the equivalent thickness for calculating the maximum deflection of a rectangular laminated glazing panel of "44-2" type as a function of both the wind load F applied on the panel, which the latter must withstand, and of the width/length ratio $\lambda$=a.b of the panel. In this example, the laminated glazing panel has a length of 3 m and comprises two glass substrates each of 4 mm thickness and two structural interlayer plies, i.e. a layer of interlayer having a thickness of 0.76 mm. FIG. 6 shows the equivalent thickness of the panel required for meeting the permissibility criteria in terms of the loading resistance of the panel, respectively for a panel with dimensions adjusted in accordance with the invention ($h_{e1}$) and for a corresponding nominal panel of the prior art ($h_{e2}$).

In the context of the invention, the expression "nominal laminated glazing panel corresponding to a laminated glazing panel according to the invention" is understood to mean a laminated glazing panel manufactured so as to withstand the same load F as the panel according to the invention, but by a conventional manufacturing method in which the equivalent thickness of the laminated glazing panel, on the basis of which the quantities representative of the loading resistance of the panel are calculated, for example using the aforementioned formulae (V) and (VI), is independent of the thickness $h_{int1}$ of the layer 3 of interlayer of the panel.

FIG. 6 clearly shows that, for the same load F that the panel must withstand, the laminated glazing panel according to the invention has a required equivalent thickness $h_{e1}$ which is equal to or greater than the required equivalent thickness $h_{e2}$ of the corresponding nominal laminated glazing panel of the prior art. Consequently, as results from formula (III) for the equivalent thickness, for the same applied load F on the panel, the laminated glazing panel according to the invention may have a smaller interlayer thickness $h_{intj}$ and/or a smaller substrate thickness $h_t$ than the interlayer thickness and the substrate thickness, respectively, of the corresponding nominal laminated glazing panel, the other dimensions of the laminated glazing panel, namely its width a, its length b and possibly whichever of its interlayer thickness and its substrate thickness that has not been reduced, being kept the same as those of the corresponding nominal laminated glazing panel.

It follows that the weight of a laminated glazing panel according to the invention, intended to withstand a predetermined load, is lower than that of a corresponding nominal laminated glazing panel of the prior art intended to withstand the same predetermined load. If the laminated glazing panel is a multi-laminated panel, the term "interlayer thickness" is understood to mean the sum of the thicknesses of the layers of interlayer of the laminated glazing panel, and the term "substrate thickness" is understood to mean the sum of the thicknesses of the substrates having a glass function of the laminated glazing panel.

FIGS. 7 to 9 illustrate the saving $\Delta h_e$ in terms of equivalent thickness, compared to the equivalent thickness of a corresponding nominal laminated glazing panel of the prior art and as a function both of the wind loading applied on the panel and of the width/length ratio $\lambda$=a/b of the panel, respectively:

in FIG. 7, for the laminated glazing panel according to the invention as considered in FIG. 6;

in FIG. 8, for a laminated glazing panel according to the invention that differs from the panel considered in FIG. 6 only in that it includes two standard interlayer plies instead of two structural interlayer plies; and in FIG. 9, for a laminated glazing panel according to the invention that differs from the panel considered in FIG. 6 only in that it comprises two acoustic interlayer plies instead of two structural interlayer plies.

It is apparent from these graphs that the equivalent thickness of a laminated glazing unit according to the invention, whatever the composition of its interlayer or interlayers, is greater than or equal to the equivalent thickness of a corresponding nominal laminated glazing unit, thereby making it possible to reduce the weight of the laminated glazing unit according to the invention, which is intended to withstand a predetermined load, compared to the corresponding nominal laminated glazing unit.

Of course, the increase in equivalent thickness of a laminated glazing unit according to the invention, although it is illustrated in the specific example of a laminated glazing panel of "44-2" type with a length of 3 m, can be transposed to other laminated glazing units, especially laminated glazing units having different dimensions a, b, $h_t$, $h_{intj}$.

As is apparent from the first and second embodiments described above, the manufacturing process according to the invention makes it possible to obtain a laminated glazing unit having both optimum loading resistance and optimum dimensions. In the context of the invention, optimum dimensions of the laminated glazing unit correspond to an optimized glass substrate and interlayer composition, so that the structure of the laminated glazing unit may be lightened compared to that of laminated glazing units manufactured using a conventional method that does not take into account the interlayer thickness in the laminated glazing. Such lightening of the structure of laminated glazing units according to the invention is particularly advantageous in the case of roof applications.

The process according to the invention allows the behavior of a laminated glazing unit in bending to be rapidly determined, whatever the characteristic time and characteristic temperature ranges of the load applied on the laminated glazing unit. This is because, once the law describing the viscoelastic behavior of the constituent material of the interlayer has been determined, on the basis of measurements made using a viscoanalyzer and of the frequency/temperature equivalence law established by the WLF method, the loading resistance of the laminated glazing unit is easily calculated using the equation expressing the transfer coefficient $\bar{\omega}$, together with analytical formulae. In particular, the process according to the invention offers the possibility of easily and rapidly determining the performance of new interlayer materials after they have been characterized by a simple viscoanalyzer measurement, without it being necessary to conduct an expensive trial.

As described above, the instructions for implementing the calculation steps of the manufacturing process according to the invention may be written onto a recording medium. The process according to the invention can then be integrated within a simplified graphical interface enabling a user to solve a laminated glazing design problem rapidly and reliably.

The invention is not limited to the examples that have been described and illustrated. In particular, the process according to the invention may be implemented for manufacturing a laminated glazing panel comprising several sheets, as illustrated by the panel 10 in FIG. 10. This panel 10 comprises three substrates having a glass function 12, 14, 16 and two layers 13, 15 of interlayer, each bonded between two substrates.

In addition, in the above examples, the laminated glazing panels comprise glass substrates and layers of PVB interlayers. More generally, the process according to the invention may be used for the manufacture of laminated glazing panels comprising substrates of any type having a glass function, especially substrates made of glass or plastic, and for the manufacture of laminated glazing panels comprising interlayers made of any viscoelastic material having suitable properties, especially materials of the acrylic polymer or acetal resin type. It is then necessary to adapt the parameters of the materials in the equation expressing the transfer coefficient.

Likewise, the invention has been described in the context of manufacturing laminated glazing panels. However, the process according to the invention may be implemented for manufacturing any laminated glazing unit, in particular laminated glazing units having a form other than a panel form, the analytical formulae for calculating the loading resistance then having to be adapted accordingly.

The invention claimed is:

1. A process for manufacturing a laminated glazing unit so that it withstands a predetermined load corresponding to a characteristic time range and to a characteristic temperature range, the laminated glazing unit including at least one substrate having a glass function and at least one layer of polymeric interlayer, the process comprising:
   determining a behavior law describing viscoelastic behavior of the constituent material of the interlayer over the characteristic time and characteristic temperature ranges of the predetermined load;
   calculating maximum value of at least one quantity representative of loading resistance of the laminated glazing unit subjected to the predetermined load, using:
      an analytical model in which the contribution of the interlayer to shear transfer in the laminated glazing unit is represented by a transfer coefficient ($\bar{\omega}$), and
      an equation expressing the transfer coefficient ($\bar{\omega}$) as a function of the Young's modulus of the interlayer, of the applied load on the laminated glazing unit, and of the dimensions of the laminated glazing unit;
   adjusting dimensions of the laminated glazing unit such that the calculated maximum value of the quantity representative of the loading resistance of the laminated glazing unit is less than or equal to a permissible maximum value;
   preparing and assembling the substrate and the layer of interlayer of the laminated glazing unit to the adjusted dimensions.

2. The manufacturing process as claimed in claim 1, wherein to determine the behavior law of the constituent material of the interlayer, the Young's modulus is measured on a sample of the interlayer using a viscoanalyzer, by varying the frequency and the temperature and by imposing a constant dynamic displacement, and the law of frequency/temperature equivalence established by the WLF (Williams-Landel-Ferry) method is used.

3. The manufacturing process as claimed in claim 1, wherein the behavior law of the constituent material of the interlayer is determined over a frequency range between $5 \times 10^{-7}$ Hz and $3 \times 10^{-1}$ Hz and a temperature (T) range between −20° C. and 60° C.

4. The manufacturing process as claimed in claim 1, wherein the following are calculated as quantities representative of the loading resistance of the laminated glazing unit:

the deflection ($w_{max}$) of the laminated glazing unit, on the basis of the equivalent thickness $h_{ef;w}$ of the laminated glazing such that:

$$h_{ef;w} = \sqrt[3]{(1-\varpi)\left(\sum_i h_i^3 + \sum_j h_{int_j}^3\right) + \varpi\left(\sum_i h_i + \sum_j h_{int_j}\right)^3},$$

and/or
   the maximum stress ($\sigma_{max}$i) on the or each substrate having a glass function of the laminated glazing unit, on the basis of the equivalent thickness $h_{ef;\sigma;i}$ of the laminated glazing, such that:

$$h_{ef;\sigma;i} = \sqrt{\frac{(h_{ef;w})^3}{(h_i + 2\varpi h_{m;i})}}$$

in which $h_i$ is the thickness of the or each substrate having a glass function;
   $h_{int_j}$ is the thickness of the or each layer of interlayer;
   $h_{m;i}$ is the distance between the mean plane of the substrate i having a glass function and the mean plane of the laminated glazing unit.

5. The manufacturing process as claimed in claim 1, wherein the equation expressing the transfer coefficient ($\bar{\omega}=f(E_{int}, F, a, b, h_i, h_{int_j})$), valid for any laminated glazing unit comprising at least one substrate having a glass function and at least one layer of polymeric interlayer, is determined according to:
   determining a behavior law describing the viscoelastic behavior of the constituent material of the interlayer of the laminated glazing unit;
   establishing a finite-element numerical model in bending of the laminated glazing unit, using the behavior law of the constituent material of the interlayer to define the mechanical properties of the interlayer;
   comparing the results obtained, on the one hand, with the numerical model and, on the other hand, with an analytical model, in which the contribution of the interlayer to shear transfer is represented by a transfer coefficient ($\bar{\omega}$), and adjusting the value of the transfer coefficient ($\bar{\omega}$) until convergence of these results;
   constructing, by successive iterations, a transfer function representative of the variation of the transfer coefficient ($\bar{\omega}$) as a function of the Young's modulus of the interlayer;
   putting the transfer function in equation form such that the transfer coefficient ($\bar{\omega}$) is expressed as a function of the Young's modulus of the interlayer, of the applied load on the laminated glazing unit and of the dimensions of the laminated glazing unit;
   determining empirically the parameters of the equation expressing the transfer coefficient ($\bar{\omega}$) as a function of the Young's modulus of the interlayer, of the applied load on the laminated glazing unit and of the dimensions of the laminated glazing unit.

6. The manufacturing process as claimed in claim 1, wherein the laminated glazing unit is a rectangular panel, the dimensions of the laminated glazing unit in the equation expressing the transfer coefficient ($\bar{\omega}=f(E_{int}, F, a, b, h_i, h_{int_j})$) being the width and the length of the panel, the thickness of the or each substrate having a glass function and the thickness of the or each layer of interlayer.

* * * * *